United States Patent
Lin et al.

(10) Patent No.: US 10,342,833 B2
(45) Date of Patent: Jul. 9, 2019

(54) **ACTIVE SUBSTANCES OF *CORDYCEPS CICADAE* AND ITS USES IN PREVENTING, DELAYING OR TREATING CATARACTS**

(71) Applicant: GRAPE KING BIO Ltd., Taoyuan (TW)

(72) Inventors: Pei-Cheng Lin, Taichung (TW); Han-Hsin Chang, Taichung (TW); Chin-Chu Chen, Taoyuan (TW); Yen-Lien Chen, Taoyuan (TW); Shu-Hsing Yeh, Taoyuan (TW); Li-Ya Lee, Taoyuan (TW); Jui-Hsia Hsu, Taoyuan (TW); Lee-Sar Sheng, Taoyuan (TW)

(73) Assignee: GRAPE KING BIO Ltd., Taoyuan (TW)

( * ) Notice: Subject to any disclaimer, the term of this patent is extended or adjusted under 35 U.S.C. 154(b) by 0 days.

(21) Appl. No.: 15/827,453

(22) Filed: Nov. 30, 2017

(65) Prior Publication Data
US 2019/0008911 A1 Jan. 10, 2019

(30) Foreign Application Priority Data
Jul. 7, 2017 (TW) .............................. 106122951 A

(51) Int. Cl.
*A61K 49/00* (2006.01)
*A01N 63/00* (2006.01)
*A61K 39/00* (2006.01)
*A61K 36/068* (2006.01)

(52) U.S. Cl.
CPC ........ *A61K 36/068* (2013.01); *A61K 2236/00* (2013.01)

(58) Field of Classification Search
CPC ........................... A61K 39/00; A61K 39/0002
USPC ...................... 424/9.1, 9.2, 93.1, 93.5, 274.1
See application file for complete search history.

(56) References Cited

FOREIGN PATENT DOCUMENTS

CA 2 912 599 10/2016

OTHER PUBLICATIONS

Weng, S.-C., et al. Journal of Ethnopharmacology, vol. 83, pp. 79-83, 2002.*
Wang, Y., et al., Brazilian Journal of Microbiology, vol. 43, No. 2, pp. 449-455, 2012.*
Ng, T.B., et al., Journal of Pharmacy and Pharmacology, vol. 57, pp. 1509-1519, 2005.*
Yue, Y., et al., Journal of Pharmacy and Pharmacology, vol. 65, No. 4, pp. 474-493.*
Tuli, H.S., et al., 3 Biotech, vol. 4, No. 1, pp. 1-12, 2014.*
Chen, Y. et al. "A 90-Day Subchronic Toxicity Study of Submerged Mycelial Culture of Cordyceps cicadae (Ascomycetes) in Rats" (2015) Int. J. Med. Mushrooms 17(8): 771-781.
Hsu, J. et al. "Healthcare Functions of Cordyceps clcadae" (2015) J. Nutr. Food Sci. 5(6): 432. doi:10.4172/2155-9600.1000432.
Chiu, C. et al. "Research and Development of Cordyceps in Taiwan" (2016) Food Science and Human Wellness 5: 177-185.

* cited by examiner

*Primary Examiner* — Rodney P Swartz
(74) *Attorney, Agent, or Firm* — Volpe and Koenig, P.C.

(57) ABSTRACT

The present invention discloses the *Cordyceps cicadae* mycelia, the active substances of *C. cicadae* mycelia, its submerged fermentation product and its pharmaceutical composition for preventing, delaying or treating cataracts, and the methods for preparing the products above. The *C. cicadae* mycelia, the active substances of *C. cicadae* mycelia, its submerged fermentation product and its pharmaceutical composition further can be prepared as a health food for preventing or delaying cataracts.

6 Claims, 7 Drawing Sheets
(3 of 7 Drawing Sheet(s) Filed in Color)

ACTIVE SUBSTANCES OF *CORDYCEPS CICADAE* AND ITS USES IN PREVENTING, DELAYING OR TREATING CATARACTS

CROSS-REFERENCE TO RELATED APPLICATION AND CLAIM OF PRIORITY

This application claims the benefit of the Taiwan Patent Application No. 106122951, filed on Jul. 7, 2017, at the Taiwan Intellectual Property Office, the disclosures of which are incorporated herein in their entirety by reference.

FIELD OF THE INVENTION

The present invention is related to an active substance. In particular, the present invention is related to the active substances of *Cordyceps cicadae* mycelia with the submerged fermentation and a pharmaceutical composition thereof for preventing, delaying or treating cataracts.

BACKGROUND OF THE INVENTION

The lens in the human eye is formed by water and fibrous proteins. The fibrous proteins are arranged in a particular manner, so that the lens is clear and light is permitted to pass through. With increasing age and due to other negative factors, fibrous proteins deteriorate and aggregate as a cluster, so that the lens becomes hardened and unclear resulting in cataracts. At this moment, it is impossible or difficult for light to pass through the lens from the cornea and project and focus on the retina. The human feels his/her vision is obscure, and cannot see any objects clearly.

Therefore, having cataracts means that the soluble proteins in the lens gradually become insoluble proteins, so the lens becomes unclear, which results in the phenomena of vision disorder, such as obscure vision, increased diopter for myopia (mild presbyopia), overlapped imaging, halation in the iris, reduced contrast vision and so on. The reasons include congenital factors, injuries, and chronic conditions, such as diabetes. The clinically most common cataracts are senile cataracts. Cataracts can be divided into nuclear cataracts, cortical cataracts, posterior subcapsular cataracts and mixed cataracts according to the sites where turbidity occurs in the lens.

Because the population is aging in developed countries and people's eyes gaze at the screen of a handheld mobile device at a short distance over long periods of time, their eyes receive high-intensity light stimulus or natural radiation, and the development of cataracts is sped up and the incidence rate of cataracts has increased globally.

Cataracts are one of the most common disorders being treated in the ophthalmology department. The patient's symptoms at the early stage include unstable vision, obscurity, diplopia, photophobia, glare at night, color change, and darkened color or distortion of the object, as well as the patient not being able to easily distinguish the brightness/darkness contrast of an object. The symptoms of late-stage cataracts are serious deterioration of vision, and blurred vision. The patient can only distinguish his fingers and the remaining light perception, and the most serious case is to cause ablepsia. Currently, there is no medicine or nutritional supplement that has been proven to effectively prevent the formation of cataracts.

Cataracts cannot be externally diagnosed by direct observation. When diagnosing cataracts, the ophthalmologist determines the shape, size and position of the opaque lens using the apparatuses, such as the slit lamp microscope, tonometer, sonicator, automatic optometry device, computer-assisted chromatic corneal topography and so on.

The current methods to prevent cataracts are to take vitamins and antioxidants, wear sun glasses to reduce the exposure to ultraviolet (UV) light, have a balanced diet and avoid smoking. However, cataract surgery is the only effective treatment.

The current clinical treatment for cataracts is to remove the unclear and opaque lens by surgery, including cataract phacoemulsification and extracapsular cataract extraction, and to implant aspherical or multi-focus artificial lens into the eye. Hyaluronan (hyaluronic acid) is used to protect the endothelium of the cornea during cataract extraction surgery. However, there is no literature to definitely indicate that hyaluronan can effectively prevent, delay or treat cataracts. Because the cost of artificial lens is not affordable by many people in the world and there are still side effects from the surgery and the risk of complications, cataracts are still the most common cause of ablepsia in humans. Therefore, undoubtedly, the development of a pharmaceutical composition and medicine for preventing, delaying or treating cataracts, or a health food for preventing or delaying cataracts has an enormous potential market.

It is therefore the Applicant's attempt to deal with the above situation encountered in the prior art.

SUMMARY OF THE INVENTION

To develop the pharmaceutical composition for preventing, delaying or treating cataracts, the *Cordyceps cicadae* mycelia, a submerged fermentation product of the *C. cicadae* mycelia, the active substances of the submerged fermentation product of the *C. cicadae* mycelia and the pharmaceutical composition thereof are prepared in the present invention. It has been proven by animal experiments that the submerged fermentation product, the active substances and the pharmaceutical composition of the *C. cicadae* mycelia can be used to effectively prevent, delay or treat cataracts. Therefore, the *C. cicadae* mycelia, and the submerged fermentation product and the active substances thereof also can be prepared as a health food for preventing or delaying cataracts.

The present invention discloses a method for preparing a pharmaceutical composition for at least one of preventing, delaying and treating cataracts, wherein the pharmaceutical composition includes an active substance of *C. cicadae*, and the method includes: (a) inoculating a *C. cicadae* mycelium on an agar plate to be incubated; (b) inoculating the incubated mycelium in step (a) into a first medium on a first scale to be incubated; and (c) inoculating the incubated mycelium in step (b) into a second medium on a second scale to be incubated to obtain a fermented product containing the active substance, wherein the second scale is larger than the first scale.

In one embodiment of the present invention, the incubation in step (a) is performed at 15~35° C. for 5~14 days, and a medium used in the agar plate in step (a) is a potato dextrose agar (PDA) medium. In one embodiment of the present invention, the incubation in step (b) is performed at 15~35° C., pH 2~8 and 10~250 rounds per minutes (rpm) for a plurality of days. In one embodiment of the present invention, the incubation in step (c) is performed in a fermentation tank having a tank pressure of 0.5~1.0 kg/cm², at 15~35° C., pH 2~8 and one of a first stirring rate and a second stirring rate, and a gas is introduced into the fermentation tank at an aeration rate of 0.01~1.5 volume per volume per minute (vvm), wherein the first stirring rate is 10~250 rpm, the second stirring rate is 0 rpm, and the gas is one selected from the group consisting of air, oxygen, carbon dioxide, nitrogen gas and a combination thereof.

In one embodiment of the present invention, the first and the second media are the same. In one embodiment of the present invention, each of the first and the second media includes one selected from the group consisting of a complex carbon and nitrogen source, an animal source of protein, a protein hydrolyzate from the animal source, a plant source of protein, a protein hydrolyzate from the plant source, a yeast extract, a malt extract, an inorganic salt, a saccharide and a combination thereof. In one embodiment of the present invention, the complex carbon and nitrogen source is one of a grain and a legume, and the inorganic salt is one selected from the group consisting of magnesium sulfate, potassium hydrogen phosphate, potassium dihydrogen phosphate, iron (III) sulfate and a combination thereof, and the saccharide is one selected from the group consisting of a glucose, a fructose, maltose, sucrose and a combination thereof.

In one embodiment of the present invention, the method further includes: (d) desiccating the fermented product, using one being selected from the group consisting of a spray drying, a heated-air drying, a roller drying, a freeze drying and a combination thereof, to obtain a dried product. In one embodiment of the present invention, the dried product is freeze-dried powder when the step (d) is performed using freeze drying.

In one embodiment of the present invention, the method further includes: (e) extracting the dried product with one of a water and an alcohol to correspondingly obtain one of a water extract and an alcohol extract. In one embodiment of the present invention, the alcohol is one of a methanol and an ethanol, the methanol has a first concentration ranged between 1% and 100%, and the ethanol has a second concentration ranging between 1% and 100%.

In one embodiment of the present invention, the pharmaceutical composition for preventing, delaying or treating cataracts includes the active substances from *C. cicadae* and the pharmaceutically acceptable carrier, excipient, diluent or adjuvant. In one embodiment of the present invention, the pharmaceutical composition for preventing, delaying or treating cataracts includes a submerged fermentation product of *C. cicadae* mycelia which contains the active substances of *C. cicadae*, and the pharmaceutically acceptable carrier, excipient, diluents or adjuvant. In one embodiment of the present invention, the pharmaceutical composition for preventing, delaying or treating cataracts includes the freeze-dried powder of the submerged fermentation product of *C. cicadae* and the pharmaceutically acceptable carrier, excipient, diluents or adjuvant. In one embodiment of the present invention, the pharmaceutical composition for preventing, delaying or treating cataracts includes a *C. cicadae* water extract or alcohol extract which contains the active substances of *C. cicadae*, and the pharmaceutically acceptable carrier, excipient, diluents or adjuvant.

The present invention further discloses a method for at least one of preventing, delaying and treating cataracts with an active substance of *C. cicadae* prepared by steps including: (a) inoculating a *C. cicadae* mycelium on an agar plate to be incubated; (b) inoculating the incubated mycelium in step (a) into a first medium on a first scale to be incubated; and (c) inoculating the incubated mycelium in step (b) into a second medium on a second scale to be incubated to obtain a fermented product containing the active substance, wherein the second scale is larger than the first scale.

The present invention further discloses an active substance of *C. cicadae* for at least one of preventing, delaying and treating cataracts being prepared by steps including: (a) inoculating a *C. cicadae* mycelium on an agar plate to be incubated; (b) inoculating the incubated mycelium in step (a) into a first medium on a first scale to be incubated; and (c) inoculating the incubated mycelium in step (b) into a second medium on a second scale to be incubated to obtain a fermented product containing the active substance, wherein the second scale is larger than the first scale.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A (Group A), "$NaCl_{(aq)}$ control"; FIG. 1B (Group B), "$NaCl_{(aq)}$ damage"; FIG. 1C (Group C), "*C. cicadae* water extract"; FIG. 1D (Group D), "Soybean oil control"; FIG. 1E (Group E), "Soybean oil damage"; and FIG. 1F (Group F), "*C. cicadae* alcohol extract".

FIG. 2A (Group A), "$NaCl_{(aq)}$ control"; FIG. 2B (Group B), "$NaCl_{(aq)}$ damage"; FIG. 2C (Group C), "*C. cicadae* water extract"; FIG. 2D (Group D), "Soybean oil control"; FIG. 2E (Group E), "Soybean oil damage"; and FIG. 2F ((Group F), "*C. cicadae* alcohol extract".

FIG. 3A (Group A), "$NaCl_{(aq)}$ control"; FIG. 3B (Group B), "$NaCl_{(aq)}$ damage"; FIG. 3C (Group C), "*C. cicadae* water extract"; FIG. 3D (Group D), "Soybean oil control"; FIG. 3E (Group E), "Soybean oil damage"; and FIG. 3F (Group F), "*C. cicadae* alcohol extract".

DETAILED DESCRIPTION OF THE PREFERRED EMBODIMENTS

Figures 1A, 1B, 1C, 1D, 1E, 1F:
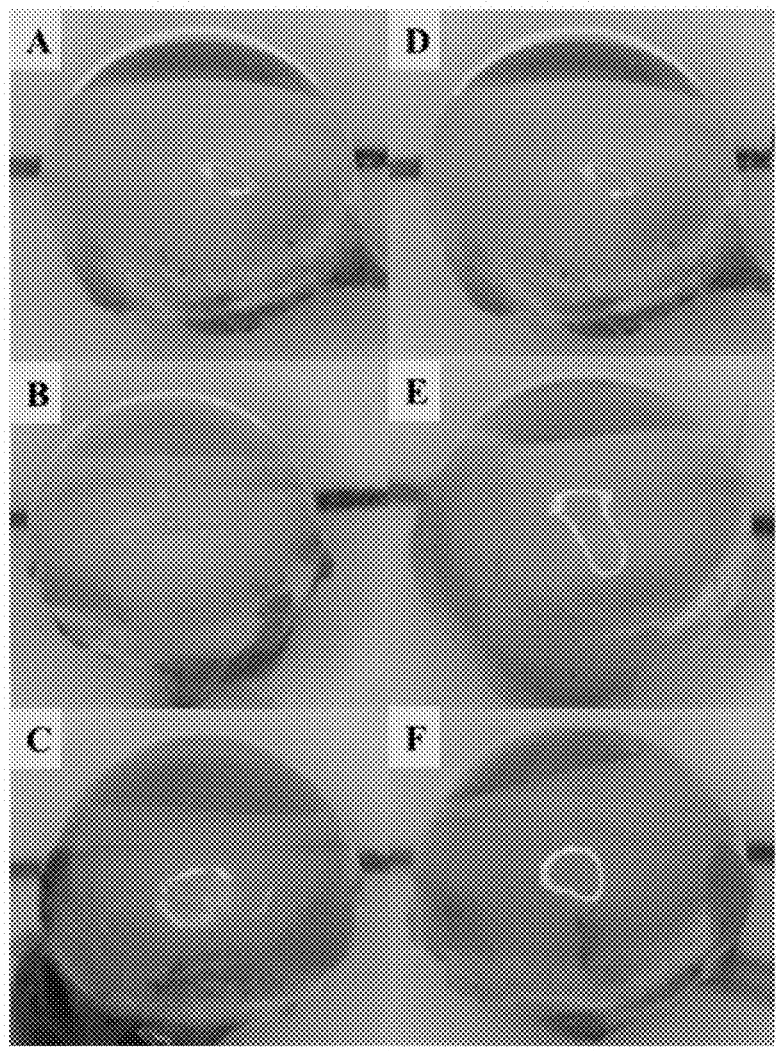
FIGS. 1A-1F illustrate panels showing the images of lenses under the scanning of a slit lamp in the present invention.
Figures 2A, 2B, 2C, 2D, 2E, 2F:
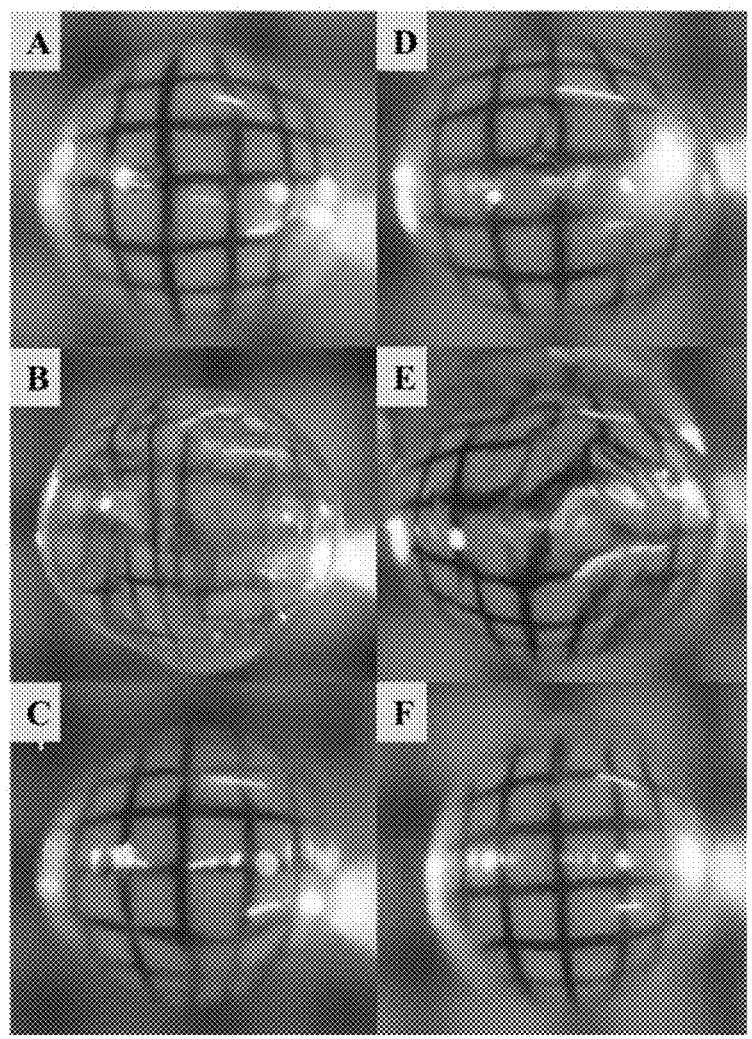
FIGS. 2A-2F illustrate panels showing the images that the lenses are disposed on the grid paper in the present invention.
Figures 3A, 3B, 3C, 3D, 3E, 3F:
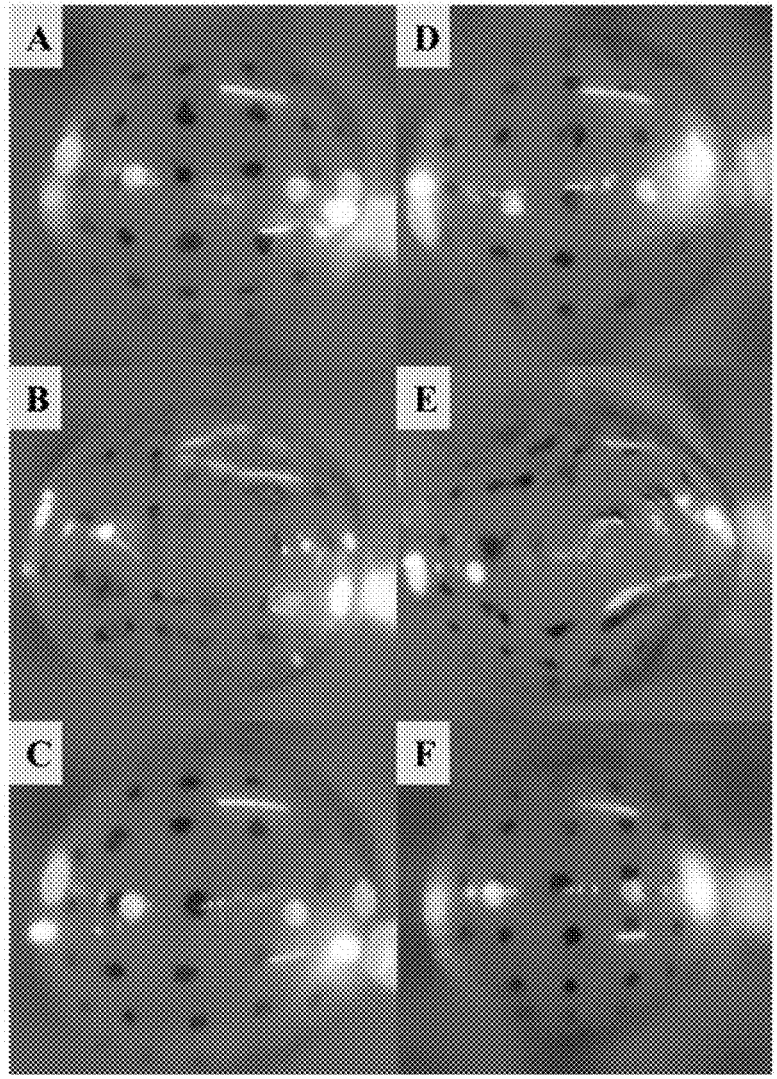
FIGS. 3A-F illustrate panels showing the images that lenses are disposed on the spot diagram in the present invention.

The present invention will now be described more specifically with reference to the following embodiments. It is to be noted that the following descriptions of preferred embodiments of this invention are presented herein for purpose of illustration and description only; they are not intended to be exhaustive or to be limited to the precise form disclosed.

*C. cicadae* is classified in the kingdom Fungi, the phylum Ascomycota, the class Sordariomycetes, the order Hypocreales, the family Clavicipitaceae and the genus *Cordyceps*. It infects cicada's pupa or the larvae of *Cicada flammate, Platypleura kaempferi, Crytotympana pustulata* and *Platylomia pieli* causing them to die, followed by the formation of an alabastrum-like stroma at the front end of the cicada's pupa or the head of the insect. Thus it looks like a flower blooming from cicada. Therefore, C. cicadae is shown as an entomopathogenic fungi. There are other species under the genus Cordyceps, such as C. sobolifera and C. cicadicola, classified according to the different hosts. Most of C. cicadae are harvested in the tropical and subtropical zones south of the Yangtze River, China, such as Fujian, Zhejiang, Sichuan, Yunnan and Jiangsu, China. The wild C. cicadae fruiting bodies are also found in some mountain areas in Taiwan.

C. cicadae is a valuable traditional herbal material. It has a cold nature, tastes sweet, and is nontoxic. It can act as a medicine after drying, and has effects on dissipating heat, relieving convulsion, exposing exthanthema. C. cicadae is mainly used to treat children's chronic convulsion, epilepsy, cardiopalmus and night crying. It is indicated by the current pharmacology that C. cicadae and its artificial culture have significant effects on immunoregulation, the regulation of nervous system, anti-fatigue, sedation, pain relief and heat dissipation, the improvement of renal functions, the reduction of blood sugar, blood pressure reduction and heart rate, the inhibition on the atherosclerosis formation, anticancer, anti-irradiation, and nourishment and fitness.

C. cicadae and Cordyceps cinensis both belong to an entomogenous fungus. The functions and applications of C. cicadae are not second to C. cinensis and Cordyceps militaris. They have similar chemical ingredients and similar pharmaceutical and health-care effects, and thus C. cicadae and C. militaris are usually used as the alternative of C. cinensis. The yields of the natural C. cinensis and C. cicadae are few, and the growth of C. cinensis and C. cicadae depends on their hosts. Furthermore, the amount of the hosts is affected by the climatic factor or anthropic factor. Accordingly, how to increase the yield of C. cicadae and its economic value is the strongest issue to be solved by the industry.

The present invention discloses a method for preparing the active substances of the submerged fermentation product of C. cicadae mycelia (abbreviated hereinafter "active substances"), a method for preparing the pharmaceutical composition containing the active substances, and a use of the active substances or the pharmaceutical composition in preventing, delaying or treating cataracts induced by physical damage. Compared to surgical excision or pharmacotherapy, the preparation method of the present invention is safer and more convenient, and the obtained active substances are more natural and safer for achieving the effect of preventing, delaying or treating ocular diseases. The active substances can also be prepared as a regular health food which is used to prevent or delay cataracts.

(I) Experimental Method

1. The Material of C. Cicadae:

The C. cicadae mycelia used in the embodiments of the present invention were obtained by harvesting the wild C. cicadae fruiting bodies in Taiwan, followed by isolating them to obtain the mycelia. The mycelia were subcultured on the agar plate, and C. cicadae was determined by identifying its genetic sequences by the Food Industry Research and Development Institute, Taiwan. However, the active substances which may be applicable in the present invention are not limited to C. cicadae.

2. The Submerged Fermentation of C. Cicadae Mycelia:

First, the C. cicadae mycelia were aseptically inoculated on the agar plate, and incubated at 15° C.~35° C. (preferably at 25° C.) for 5 days to 2 weeks (14 days). Subsequently, the C. cicadae mycelia were aseptically scraped from the plate and inoculated in the medium with a first scale (such as the medium in a flask), followed by incubating at 15° C.~35° C. (preferably at 25° C.), pH 2~8 (preferably pH 4~7, and more preferably about pH 4.5) and a shaking rate of 10~250 rounds per minute (rpm) for several days (such as 3 days or more). Next, the incubated product in the flask was aseptically inoculated in the medium with a second scale (such as the medium in a fermentation tank), and incubated at 15° C.~35° C. (preferably at 25° C.), a tank pressure of 0.5~1.0 $kg/cm^2$, pH 2~8, an agitation rate of 10 rpm~150 rpm or air lift and an aeration rate of a gas (such as air, a mixture of air, oxygen, carbon dioxide or nitrogen) of 0.01~1.5 volume per volume per minute (vvm) for 3 days to 5 days, to obtain a submerged fermentation product of C. cicadae mycelia, which contains C. cicadae mycelia and the supernatant. The submerged fermentation product of C. cicadae mycelia contains the active substances from C. cicadae. To enlarge the yield of the submerged fermentation product of C. cicadae mycelia, the second scale is usually larger than the first one. The gas at the aeration rate of 0.01~1.5 vvm preferably is air.

The media with the first scale and the second scale may include the same or different components and formulae. The media with the first scale and the second scale may use, but not be limited to, the formula shown in Table 1.

TABLE 1

The formula of the media

| Component | Amount (wt. %) |
| --- | --- |
| Complex carbon and nitrogen source | 0.01~5 |
| Animal or plant sources of protein or its hydrolyzate | 0.01~2 |
| Yeast or melt extract thereof (powder or cream) | 0.001~2 |
| Inorganic salt | 0.0001~0.05 |
| Saccharide | 0.01~10 |
| Water | Add to 100 wt. % |

The complex carbon and nitrogen source may be grain (e.g. flour) or legume (e.g. soybean flour, mung bean flour and so on), the inorganic salt may be magnesium sulfate, potassium hydrogen phosphate, potassium dihydrogen phosphate, iron (III) sulfate and so on, and the saccharide may be glucose, fructose, maltose, sucrose and so on.

3. The Dryness of the Submerged Fermentation Product of C. Cicadae Mycelia:

The submerged fermentation product of C. cicadae mycelia may be further dried as the freeze-dried powder. The drying techniques used may include but not limited to spraying drying, hot-air drying, roller drying, freeze drying or other conventional drying techniques suitable for the present invention.

4. The Extraction of the Submerged Fermentation Product of C. Cicadae Mycelia:

The freeze-dried powder of the submerged fermentation powder of C. cicadae mycelia was added to distilled water, dissolved and suspended in the distilled water followed by heating for several minutes at 90° C.~121° C. After cooling, the sample was concentrated under reduced pressure or was subjected to the drying technique above to obtain the water extract of C. cicadae mycelia (abbreviated as the C. cicadae water extract).

Alternatively, the freeze-dried powder of the submerged fermentation powder of *C. cicadae* mycelia was added to and suspended in alcohol (e.g. 1% (v/v)~100% (v/v) methanol or ethanol), followed by immersing, stirring or sonicating for extraction for several minutes. The reaction mixture was concentrated under reduced pressure or was subjected to the dryness technique above to obtain the alcohol extract of *C. cicadae* mycelia (abbreviated as the *C. cicadae* alcohol extract).

5. The Preparation of the Pharmaceutical Composition Containing the Active Substances of *C. Cicadae*:

Depending on his/her knowledge and techniques in pharmacology, the skilled person in the art can prepare the pharmaceutical composition for preventing, delaying or treating cataracts using the active substances of *C. cicadae*, the submerged fermentation product of *C. cicadae* containing the *C. cicadae* active substances, the lyophilizer containing the *C. cicadae* active substances, or the *C. cicadae* water or alcohol extract containing the *C. cicadae* active substances, and the pharmaceutically acceptable carrier, excipient, diluent or adjuvant. The dosage form of the pharmaceutical composition can include but is not limited to the capsule, tablet, pill, emulsion, suspension dispersant and solution. Taking the tablet as an example, the pharmaceutically acceptable carrier includes but is not limited to lactose, corn starch, lubricant and magnesium stearate. The diluent used in the capsule includes but is not limited to lactose and dried corn starch.

6. The Preparation of the Health Food Containing the *C. Cicadae* Active Substances:

Depending on his/her knowledge and techniques in the food industry, the skilled person in the art can prepare the health food for preventing or delaying cataracts using the *C. cicadae* active substances, the submerged fermentation product of *C. cicadae* containing the *C. cicadae* active substances, the lyophilizer containing the *C. cicadae* active substances, or the *C. cicadae* water or alcohol extract containing the *C. cicadae* active substances, and the food-grade additives (such as the extender, colorant, sweetener, flavor, preservative and so on).

(II) Animal Experiments

Ultraviolet (UV) is divided into UVA (315~380 nm), UVB (280~315 nm) and UVC (100~280 nm) according to the wavelength. Over-irradiation by UV may result in photochemical damage, in particular the damage to eyeballs. The corneas can absorb most UVC, but the transmittance of the corneas will be rapidly increased to the UV of the longer wavelength. For instance, 60% of 320-nm UV may transmit through the cornea. The lens further absorbs most UV which irradiates into the eye. Young people's lenses can absorb UV lower than the 370-nm wavelength. However, elderly people's lenses may become yellowish-brown and absorb more UVA and blue light with shorter wavelength.

It is proven by animal experiments that UV irradiation can cause cataracts, and in particular opacity may occur easily at the cortex and posterior subcapsule of the lens. It can be observed under a microscope that the undifferentiated epithelial cells of the lens move backwards to cause posterior subcapsular opacity cataracts. The occurrence of cataracts is related to exposure to sunlight according to the epidemiological research and clinical observation. People who live close to the equator or the higher sunshine area and do more outdoor exercise may have higher incidences of cataracts. Further research shows that cataracts are related to UVB irradiation, and opacity mostly occurs at the cortex and the posterior subcapsule of the lens.

In the present invention, the lens damage in mice was induced by UV to evaluate the effect of the *C. cicadae* active substances on preventing, delaying or treating the UV-induced cataracts, and their relevant applications on eye protection.

Example 1: The Submerged Fermentation and the Preparation of the *C. Cicadae* Active Substances 1. Incubation on the Plate:

The *C. cicadae* mycelium was aseptically inoculated on a potato dextrose agar (PDA) plate and incubated at 25° C. for about 5 days.

2. Incubation in the Flask:

The *C. cicadae* mycelium was aseptically scraped from the incubated plate, inoculated into the medium (containing 2.0 weight % (wt. %) sucrose, 0.5 wt. % yeast extract, 1.0 wt. % soybean flour, and water is added to 100 wt. %) of the flask, and incubated with shakes of 120 rpm at 25° C., pH 4.5 for 3 days.

3. Incubation in the Fermentation Tank:

The *C. cicadae* mycelia in the flask was aseptically inoculated into the medium of the fermentation tank. The ingredients of the medium in the fermentation tank are the same as those in the flask. Incubation and fermentation were performed at 25° C., a tank pressure of 0.5~10 $kg/cm^2$, pH 4.5, a stirring rate of 10 rpm~150 rpm or 0 (air lift), and an aeration rate of a gas of 0.5~1.0 vvm for 3 days to obtain the submerged fermentation product of the *C. cicadae* mycelia, which includes the *C. cicadae* mycelia and the supernatant. The submerged fermentation product of *C. cicadae* mycelia contains the active substances originated from *C. cicadae*. The submerged fermentation product of *C. cicadae* mycelia was further freeze-dried to obtain the freeze-dried powder for reservation. The submerged fermentation product of *C. cicadae* mycelia from a 20-ton fermentation tank was subjected to freeze drying to obtain about 110 kg freeze-dried powder.

4. The Preparation of the *C. Cicadae* Water Extract:

The freeze-dried powder of *C. cicadae* mycelia was dissolved in 20× volume distilled water, and heated at 100° C. for 30 minutes. After cooling, freeze drying was carried out to obtain the *C. cicadae* water extract.

5. The preparation of the *C. cicadae* alcohol extract:

The freeze-dried powder of *C. cicadae* mycelia was dissolved in 20× volume ethanol (1%~100% ethanol), and extracted by sonication for 1 hour. The extraction suspension was centrifuged to obtain the supernatant, which was further concentrated under reduced pressure to obtain the *C. cicadae* alcohol extract. The 1% ethanol or <100% ethanol means that ethanol was mixed with the solvent (such as water) by volume, and 100% ethanol refers to the pure ethanol without supplementing any solvent (such as water). The skilled person in the art can replace methanol or ethanol by a compound having the physical and chemical properties similar to methanol or ethanol.

Embodiment 2: The Animal Model for Cataracts and the Analysis for the Relevant Indexes 1. The Establishment of the Mouse Model for Cataracts:

In this embodiment, female ICR mice at 6-week age and 25~33 g of body weight were purchased from BioLASCO Taiwan Co., Ltd. (Taipei, Taiwan) and bred in the Experimental Animal Center, Chung Shan Medical University, Taichung, Taiwan. A regular diet and clean water were provided, and the light cycle was 12-hours light followed by 12-hours dark. The temperature and the humidity were controlled at 20±2° C. and 50±5%, respectively.

2. The Dosage, the Administration and the Experimental Steps:

The UVB irradiated from a UV lamp (tube model: VL-6MCUVB, Vilber Lourmat, France) induced cataracts in the mice. The experiment was carried out for 29 days, and the mice were randomly divided into 6 groups before the experiment, each for 3 mice.

(1) "$NaCl_{(aq)}$ control" group: feeding 0.9% NaCl aqueous solution daily via a feeding tube;

(2) "$NaCl_{(aq)}$ damage" group: feeding 0.9% NaCl aqueous solution daily via the feeding tube, and irradiating UVB to cause damage from days 6~28;

(3) "*C. cicadae* water extract" group: feeding 100 mg *C. cicadae* water extract (dissolved in 0.9% NaCl aqueous solution) per kilogram body weight daily, and irradiating UVB to cause damage from days 6~28;

(4) "Soybean oil control" group: feeding the commercial soybean oil daily;

(5) "Soybean oil damage" group: feeding the commercial soybean oil daily, and irradiating UVB to cause damage from days 6~28; and (6) "*C. cicadae* alcohol extract" group: feeding 100 mg *C. cicadae* alcohol extract (dissolved in the commercial soybean oil) per kilogram body weight daily, and irradiating UVB to cause damage from days 6~28.

In the UVB-treatment groups (i.e. "$NaCl_{(aq)}$ damage", "*C. cicadae* water extract", "soybean oil damage" and "*C. cicadae* alcohol extract"), mice were kept in a dark box after anesthetizing with 2.5% avertin, their eyeballs were faced upward to receive 0.72 J/cm$^2$ UV for 90 seconds to hurt the mice's lenses. Mice in all groups were sacrificed on day 29.

3. The Measurement of the Lenses' Damage and the Analysis of Relevant Indexes to Evaluate Cataracts:

These experiments are to measure the images of the eyeball (using the slit lamp) and the lens (using the grid paper and the spot diagram).

The purpose of comparing the slit lamp-scanned images is to determine the light transmittance of the lens inside the eyeball by the laterally projected light, and further to determine the progress of the cataracts and the definition of the image. After being sacrificed, the mouse's right eyeball was disposed on a white-background board (which has a red line thereon), the corneal limbus was aligned to the red line, and the image of the lateral side of the right eyeball was pictured.

The lens' images further include an image showing the grid paper (abbreviated as "the grid-paper image") and an image showing the spot diagram (abbreviated as "the spot-diagram image"). The main purpose to compare grid-paper images is to determine whether the image of the central area of the lens is normal, and the main purpose to compare spot-diagram images is to determine whether the image of the peripheral area of the lens is excellent. After being sacrificed, the lens of the mouse's left eyeball was disposed on a grid paper or a spot diagram, and the image of the lens of the right eyeball was pictured.

4. The Analysis of the Penetration Rate and the Light Transmittance Using the Photometer:

The purposes of the penetration rate and the light transmittance are to determine the differences of the resistance to injury between the UVB-damaged lens and the lens where the mouse was fed with the *C. cicadae* active substances in advance.

The penetration rate is to determine the percentage of light that passes through the lens at different wavelengths using a photometer. The lens of the mouse's left eyeball was disposed on a slide and above a sensing probe of the photometer. The lens was irradiated by a fixed light source, and the penetration rate and the light transmittance were determined.

The measurement of light transmittance is to calculate how many lumens of light passes through the lens. The less light to pass through means that the transparency of the lens is lower, the severity of cataracts is higher, and thus the lumens of light which passes through the lens is decreased. The transmittance of the lens is obtained by subtracting the lumens of the light (which passes through the lens) from the total lumens of the light in the beginning (i.e. the full-wavelength light). The higher transmittance of the lens refers to the lower difference of the lumens. Therefore, the severity of cataracts can be represented by the difference of the lumens.

Example 3: The Evaluation and Effect of the *C. Cicadae* Active Substances on Preventing, Delaying and Treating Cataracts 1. The Measurements of the Eyeball's Image (Using the Slit Lamp) and the Lens' Image (Using the Grid Paper and the Spot Diagram)

Please refer to FIG. 1, which illustrates panels showing the images of lenses under the scanning of a slit lamp in the present invention. In FIG. 1, the abnormal characteristics for the lens are not shown in the "$NaCl_{(aq)}$ control" (A) and "soybean oil control" (D) groups. On the contrary, the unclear lenses are shown in the "$NaCl_{(aq)}$ damage" (B) and "soybean oil damage" (E) groups, indicating that UVB successfully induces cataracts in mice. In the groups (C and F) that had mice that were fed with the *C. cicadae* water and alcohol extracts, both extracts can effectively maintain the transmittance of the lateral side of the mouse's eyeball. Therefore, the *C. cicadae* water extract and the *C. cicadae* alcohol extract containing the *C. cicadae* active substances and the prepared pharmaceutical composition can effectively prevent, delay or treat cataracts induced by physical damage.

Please refer to FIGS. 2A-F, which illustrate panels showing the images where the lenses are disposed on the grid paper in the present invention. In FIGS. 2A-F, in addition to observing the results similar to the comparison of the image of lens (FIGS. 1A-F), when the image definition at the central area of the lens is compared with the distortion of the grid-paper image, it is found that the "$NaCl_{(aq)}$ control" (A, FIG. 2A) and "soybean oil control" (D, FIG. 2D) groups show the clear grid-paper images where distortion and contortion almost are not shown, and the "$NaCl_{(aq)}$ damage" (B, FIG. 2B) and "soybean oil damage" (E, FIG. 1E) groups both show the indefinite grid-paper images where distortion and contortion occur. However, the "*C. cicadae* water extract" (C, FIG. 1C) and "*C. cicadae* alcohol extract" (F, FIG. 1C) groups show the definite grid-paper images where distortion and contortion are almost not shown. Therefore, the *C. cicadae* water and alcohol extracts containing the *C. cicadae* active substances and the prepared pharmaceutical composition can effectively prevent, delay or treat cataracts induced by physical damage.

Please refer to FIGS. 3A-F, which illustrate panels showing the images where lenses are disposed on the spot diagram in the present invention. The dot-diagram images for the lens' peripheral area in FIGS. 3A-F also show the results consistent with the grid-paper images for the lens in FIGS. 2A-F. Therefore, feeding the *C. cicadae* water or alcohol extract in advance can prevent, delay or treat the UVB-induced damage on early-stage cataracts.

Figure 4:
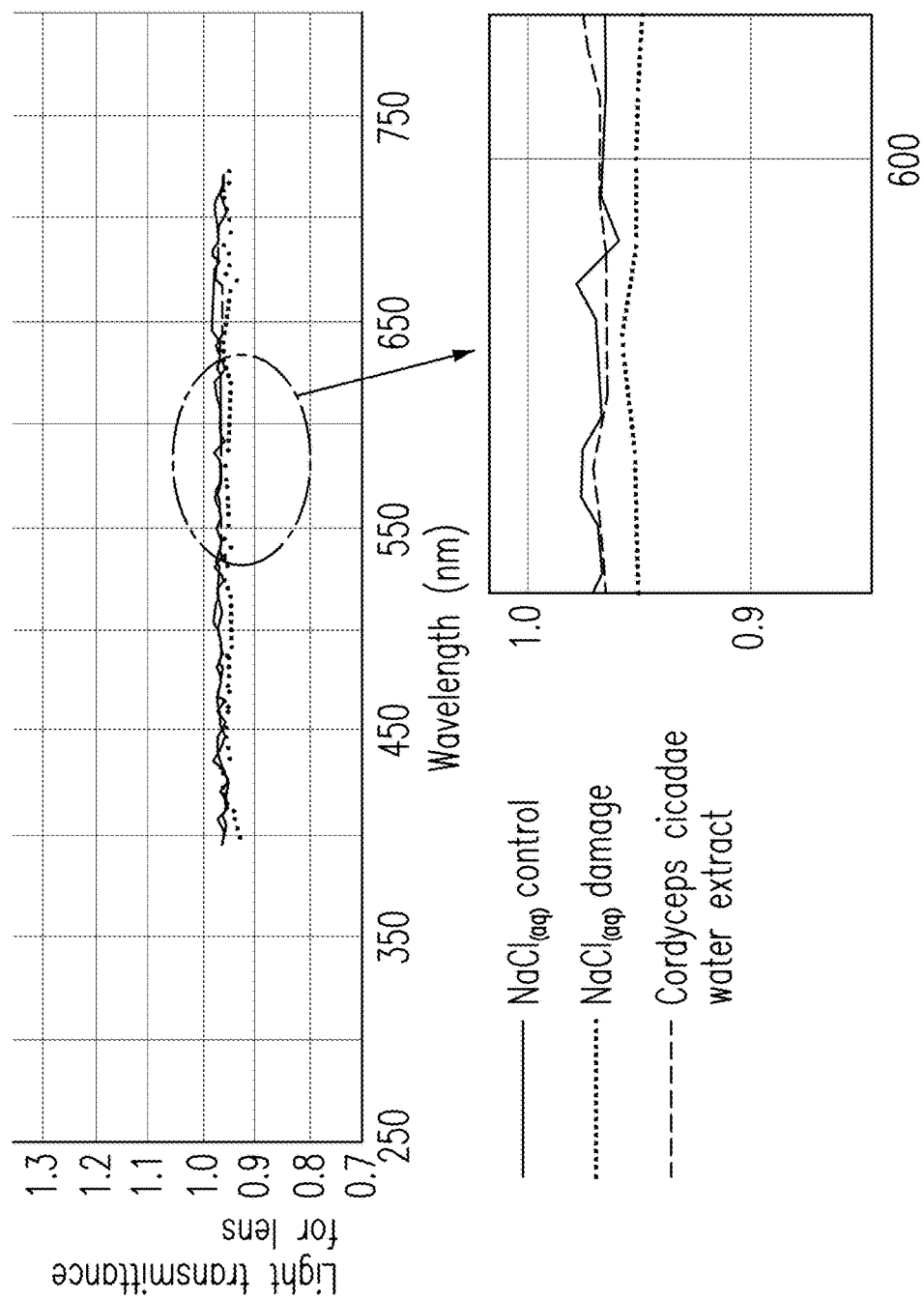
FIG. 4 illustrates a diagram showing the light transmittance of the lenses in mice which were fed with the *C. cicadae* water extract of the present invention.
Figure 5:
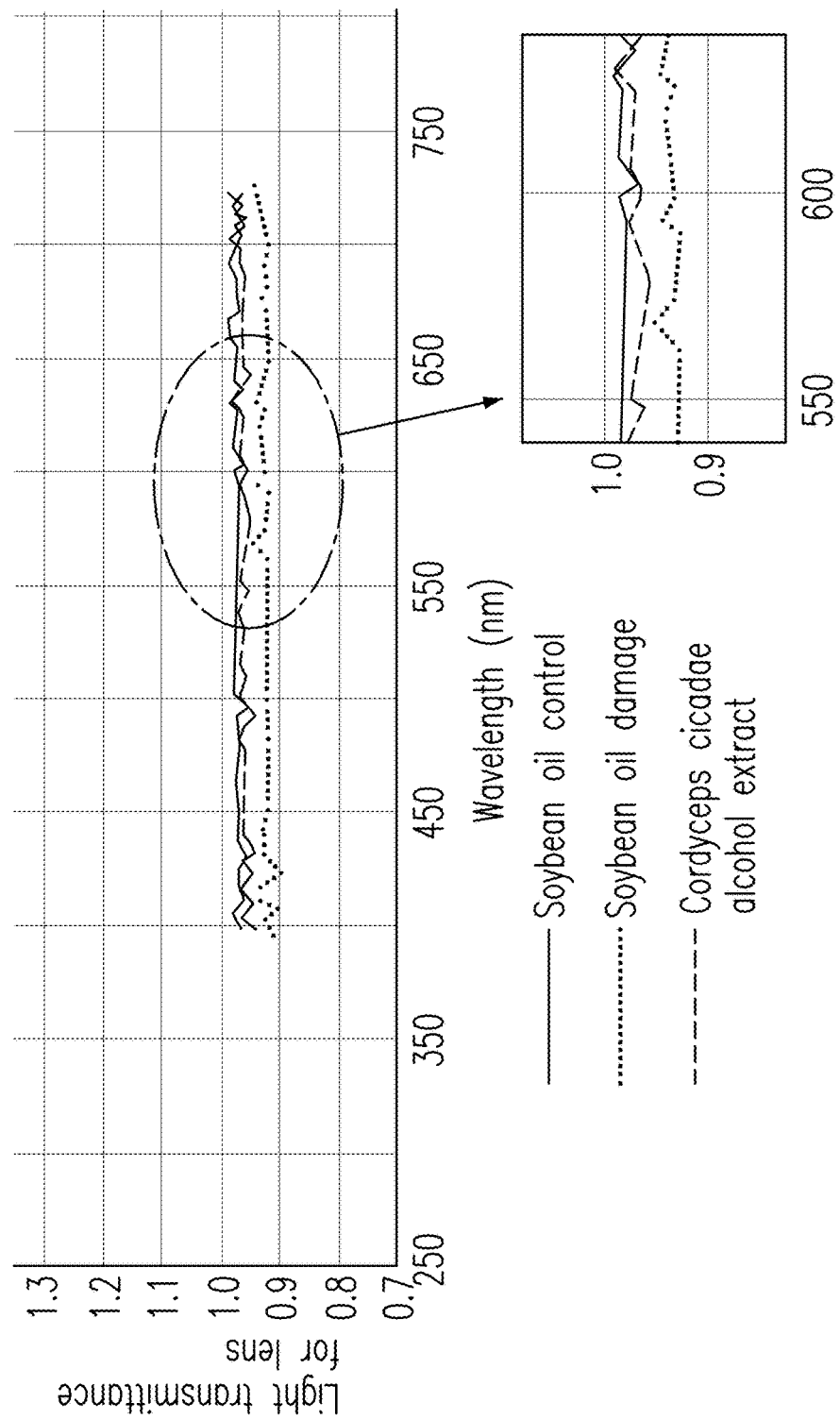
FIG. 5 illustrates a diagram showing the light transmittance of the lenses in mice which were fed with the *C. cicadae* alcohol extract of the present invention.

2. The Analysis of the Penetration Rate and the Light Transmittance Using the Photometer:

Please refer to FIGS. 4 and 5, which respectively illustrate the diagrams showing the light transmittance of the lenses in mice which were fed with the *C. cicadae* water extract and the *C. cicadae* alcohol extract of the present invention. In FIGS. 4 and 5, lenses were irradiated with a fixed warm-white light source at 400~725 nm, and the light transmittances at 550~600 nm were compared among groups (referring to the partial enlargement diagrams). The results are consistent with those in the slip-lamp scanning images (FIGS. 1A-F) and the grid-paper images (FIGS. 2A-F and 3A-F). The "$NaCl_{(aq)}$ control" and "soybean oil control" groups show the consistent patterns on light transmittance, and the same as the "*C. cicadae* water extract" and "*C. cicadae* alcohol extract" groups. Therefore, feeding the *C. cicadae* water or alcohol extract in advance can maintain the transmittance of the UVB-damaged lenses in mice and make the imaging more definite. Therefore, feeding the *C. cicadae* water or alcohol extract in advance can prevent, delay or treat the UVB-induced damage on early-stage cataracts.

Figure 6:
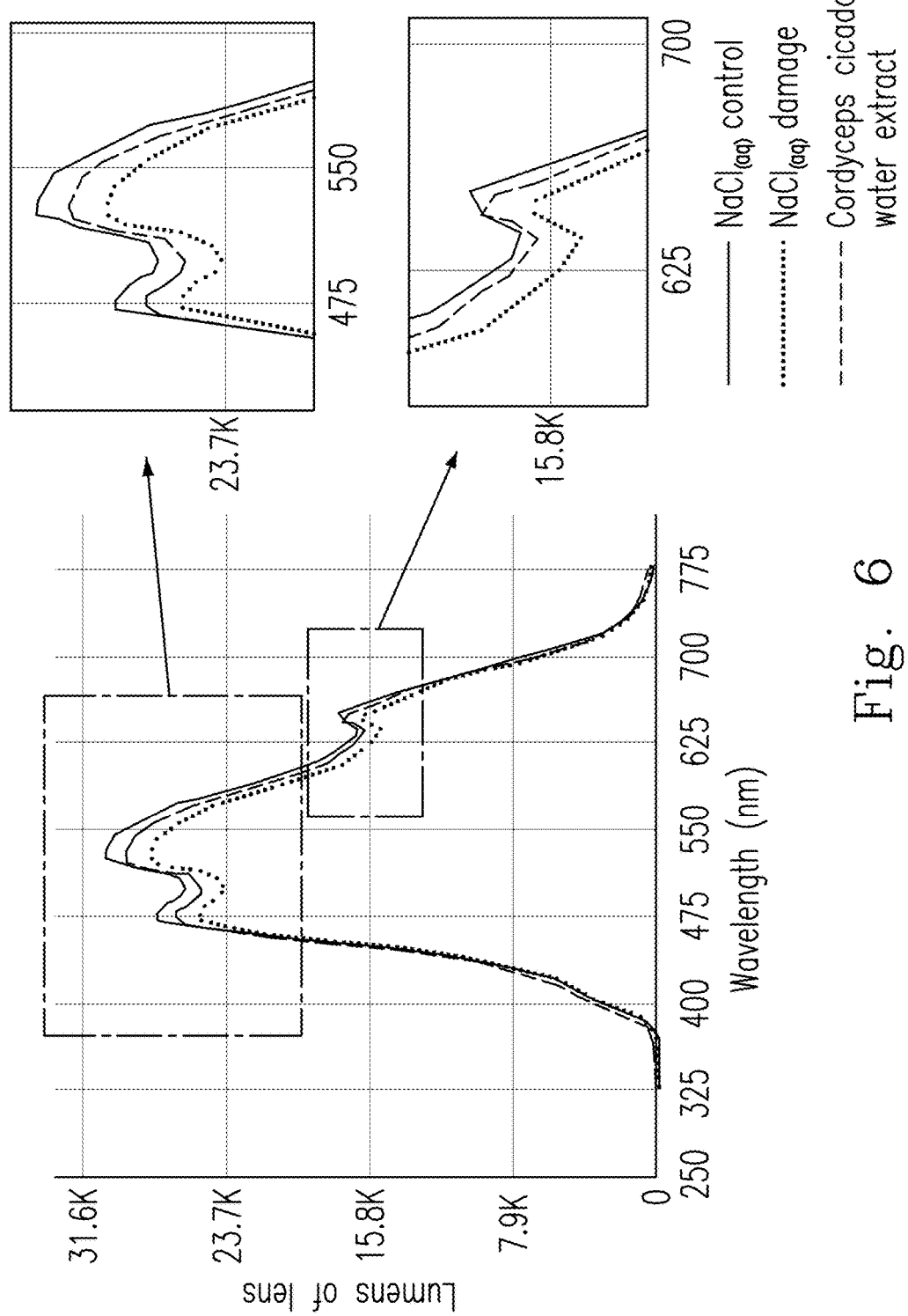
FIG. 6 illustrates a diagram showing the lumen of the lenses in mice which were fed with the *C. cicadae* water extract of the present invention.
Figure 7:
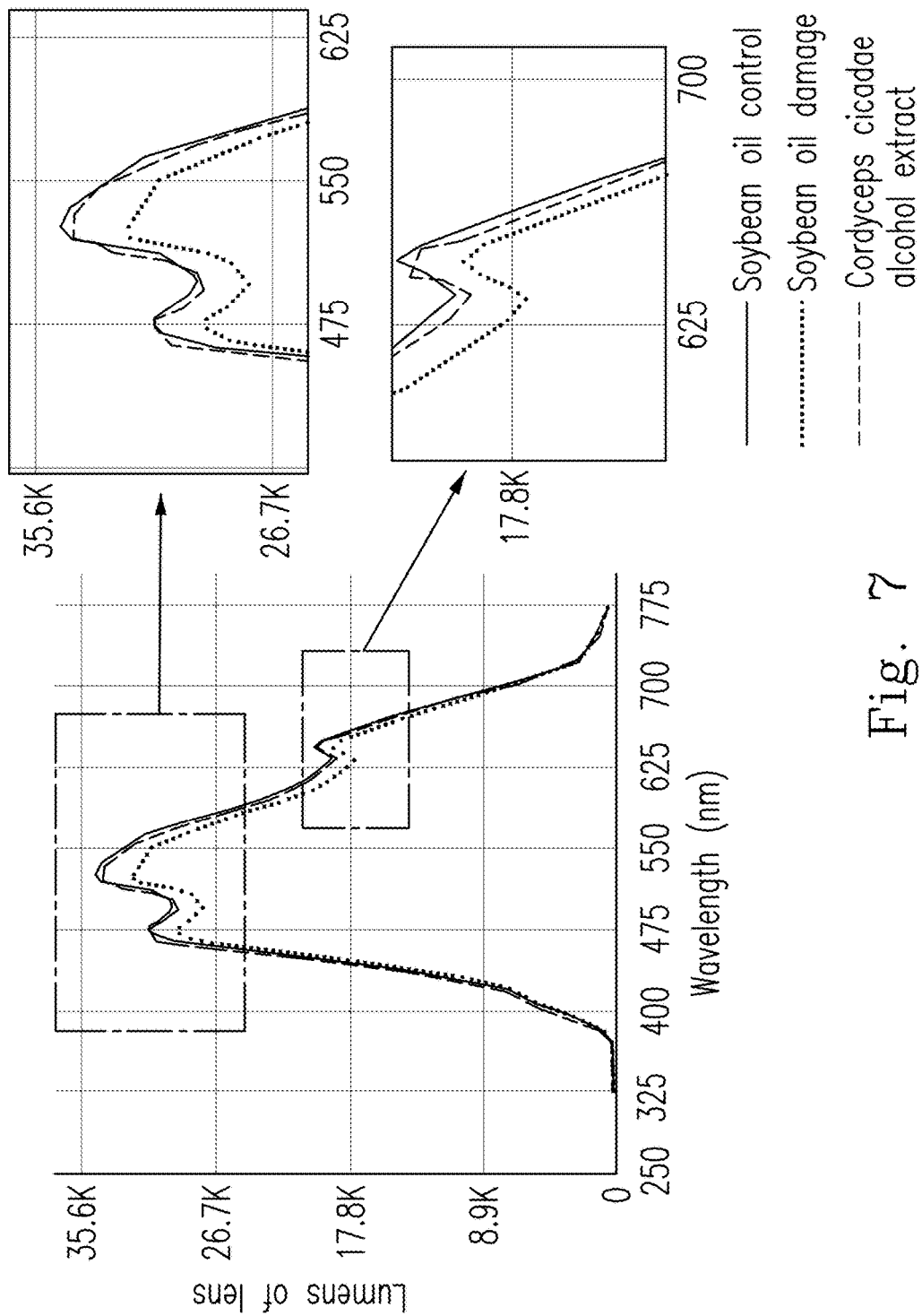
FIG. 7 illustrates a diagram showing the lumen of the lenses in mice which were fed with the *C. cicadae* alcohol extract of the present invention.

Please refer to FIGS. 6 and 7, which respectively illustrate the diagram showing the lumen of the lenses in mice which were fed with the *C. cicadae* water extract and the *C. cicadae* alcohol extract of the present invention. In FIGS. 6 and 7, the differences of lumens at 425~550 nm and 600~650 nm were compared among groups (referring to the partial enlargement diagrams). FIGS. 6 and 7 show the results similar to the above. That is, even though mice which were fed with the *C. cicadae* water and alcohol extracts in advance were damaged by UVB, their lenses' transmittance can still be maintained. Therefore, the *C. cicadae* water or alcohol extract containing the *C. cicadae* active substances and the prepared pharmaceutical composition can effectively prevent, delay or treat the UV-induced damage of the cataracts.

In conclusion, the *C. cicadae* mycelia, the submerged fermentation product (and the freeze-drying powder) of *C. cicadae* mycelia, the active substances of the submerged fermentation product of *C. cicadae* mycelia and the pharmaceutical composition prepared using the above products can effectively prevent, delay or treat cataracts and cataracts induced by UV damage. Accordingly, the *C. cicadae* mycelia, the submerged fermentation product (and the freeze-drying powder) of *C. cicadae* mycelia, the active substances of the submerged fermentation product of *C. cicadae* mycelia also can be prepared as the health food for preventing or delaying cataract according to a health food manufacturing techniques in this art.

While the invention has been described in terms of what is presently considered to be the most practical and preferred Embodiments, it is to be understood that the invention need not be limited to the disclosed Embodiments. On the contrary, it is intended to cover various modifications and similar arrangements included within the spirit and scope of the appended claims, which are to be accorded with the broadest interpretation so as to encompass all such modifications and similar structures.

What is claimed is:

1. A method for reducing formation of cataracts induced by UVB damage in a subject, comprising:
   administering to the subject a therapeutically effective amount of a water or alcohol extract of *Cordyceps cicadae*.

2. The method according to claim 1, wherein the water or alcohol extract of the *Cordyceps cicadae* is prepared by a method comprising:
   (a) inoculating a *C. cicadae* mycelium on an agar plate to be incubated;
   (b) inoculating the incubated mycelium in step (a) into a first medium on a first scale to be incubated;
   (c) inoculating the incubated mycelium in step (b) into a second medium on a second scale to be incubated to obtain a fermented product, wherein the second scale is larger than the first scale;
   (d) desiccating the fermented product, by using one being selected from the group consisting of a spray drying, a heated-air drying, a roller drying, a freeze drying and a combination thereof, to obtain a dried product; and
   (e) extracting the dried product with one of a water and an alcohol to correspondingly obtain the water or alcohol extract of the *Cordyceps cicadae*.

3. The method according to claim 1, wherein the subject suffers from the cataracts.

4. The method according to claim 2, wherein the incubation in step (a) is performed at 15~35° C. for 5~14 days.

5. The method according to claim 2, wherein the incubation in step (b) is performed at 15~35° C., pH 2~8 and 10~250 rounds per minutes (rpm) for a plurality of days.

6. The method according to claim 2, wherein the incubation in step (c) is performed in a fermentation tank having a tank pressure of 0.5~1.0 $kg/cm^2$, at 15~35° C., pH 2~8 and one of a first stirring rate and a second stirring rate, and a gas is introduced into the fermentation tank at an aeration rate of 0.01~1.5 volume per volume per minute (vvm), wherein the first stirring rate is 10~250 rpm, and the second stirring rate is 0 rpm.

* * * * *